(12) United States Patent
Hasegawa et al.

(10) Patent No.: US 7,576,169 B2
(45) Date of Patent: Aug. 18, 2009

(54) FACILE SYNTHESIS OF POLYHEDRAL SILSESQUIOXANE ANIONS AND USE THEREOF

(75) Inventors: Isao Hasegawa, Gifu (JP); Richard M. Laine, Ann Arbor, MI (US); Michael Z. Asuncion, Ann Arbor, MI (US); Norihiro Takamura, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 752 days.

(21) Appl. No.: 10/971,809

(22) Filed: Oct. 22, 2004

(65) Prior Publication Data

US 2005/0142054 A1 Jun. 30, 2005

Related U.S. Application Data

(60) Provisional application No. 60/513,665, filed on Oct. 23, 2003.

(51) Int. Cl.
*C08G 77/04* (2006.01)
*C08G 77/06* (2006.01)
*C01B 33/113* (2006.01)

(52) U.S. Cl. ............................. 528/33; 423/325; 428/12

(58) Field of Classification Search ................ 423/325; 528/12, 33
See application file for complete search history.

(56) References Cited

U.S. PATENT DOCUMENTS 5,047,492 A 9/1991 Weidner et al.
5,330,734 A 7/1994 Johnson et al.
6,288,257 B1 * 9/2001 Schattenmann et al. ..... 556/470

OTHER PUBLICATIONS

Hasegawa, Isao and Sumio Sakka. "Rapid Solidification of (2-Hydroxyethyl)trimethylammonium Silicate," Chemistry Letters. 1988, pp. 1319-1322.*
D. Hoebbel et al., Zeitschrift Für Anorganische Und Allgemeine Chemie, 384, pp. 43-52 (1971).
I. Hasegawa et al., Journal of Molecular Liquids, 34, pp. 307-315 (1987).
Hasegawa et al., J. Organometallic Chem., 441, pp. 373 (1992).
Hoebbel et al., Die Konstitution des Tetramethylammoniumsilicats de Zusammensetxung 1,0 N(C3)4OH 1, 0 SiO2 8,0-8,3 H2O; Z. anorg. allg. Chem., 384, English Abstract and pp. 43-52 (1971).
Hoebbel et al., Synthese, Aufbau und Eigenschaften kafigartiger vinyl- und allyisilylierter Kieselsauren; Z. anorg. allg. Chem. 578 (1989), English Abstract and pp. 160-168.

* cited by examiner

*Primary Examiner*—Jerry Lorengo
*Assistant Examiner*—Kevin M Johnson
(74) *Attorney, Agent, or Firm*—Brooks Kushman P.C.

(57) ABSTRACT

Polyhedral silsesquioxane anions are economically prepared by reaction of a silica source derived from combusted organic material with a quaternary ammonium hydroxide compound. Reaction of the resulting anions with chlorosilanes may be effected in near stoichiometric fashion in organic solvent containing reactive quantities of organic acids such as formic acid. The functional groups on the resulting functionalized silsesquioxanes may be substituted for other functional groups by reaction with di- or polysiloxanes in the presence of a synthetic ion exchange resin.

9 Claims, No Drawings

FACILE SYNTHESIS OF POLYHEDRAL SILSESQUIOXANE ANIONS AND USE THEREOF

CROSS-REFERENCE TO RELATED APPLICATIONS

This application claims the benefit of U.S. provisional application Ser. No. 60/513,665 filed Oct. 23, 2003, which is herein incorporated by reference.

BACKGROUND OF THE INVENTION

1. Field of the Invention

The present invention pertains to an economically viable synthesis of silsesquioxane anions and their derivatives, and to the use thereof.

2. Background Art

Silsesquioxane anions, particularly the cubeoctameric $Si_8O_{20}^{8-}$ anion, are known. These polyhedral anions, having the general formula $Si_nO_{5n/2}^{n-}$, may be prepared by hydrolyzing organosilicates such as tetraethoxysilane (tetraethylsilicate) in the presence of a quaternary ammonium compound such as tetramethylammonium hydroxide, as described in D. Hoebbel et al., ZEITSCHRIFT FÜR ANORGANISCHE UND ALLGEMEINE CHEMIE, 384, pp. 43-52 (1971); I. Hasegawa et al., JOURNAL OF MOLECULAR LIQUIDS, 34, pp. 307-315 (1987); and Weidner et al. U.S. Pat. No. 5,047,492. Synthesis from fumed silica or precipitated silica employing quaternary ammonium compounds in aqueous medium is also known, as also disclosed in U.S. Pat. No. 5,047,492.

The silsesquioxane anions can serve as useful precursors to numerous polyhedral silsesquioxanes bearing reactive and/or non-reactive functional groups. Examples are octakis[vinyldimethylsiloxy]octasilsesquioxane, octakis[hydridodimethylsiloxy]octasilsesquioxane, and silsesquioxanes with mixed hydrido and vinyldimethylsiloxy functionalities which can serve as useful monomers in polymer synthesis, and as nuclei for a variety of functionalized "star" compounds or "dendrimeric" compounds.

Unfortunately, prior syntheses have been costly, as well as time and energy intensive. Organosilicates and fumed silicas, for example, generally employ tetrachlorosilane, $SiCl_4$ or organohalosilanes as starting materials. $SiCl_4$ and organohalosilanes, in turn, are prepared from metallic silicon which in turn is prepared by carbothermal reduction of $SiO_2$. The expense of these starting materials precludes use of the silsesquioxane anions and derivatives prepared therefrom in all but the most demanding applications. Precipitated silica preparation is also energy intensive, involving reacting quartz sand with sodium carbonate at high temperature (1200° C.), dissolving the resulting sodium silicate in water, followed by neutralization with strong acid. Furthermore, preparation of silsequioxane anions from crystalline silica or low surface area silica is a time consuming reaction which is therefore capital and time intensive.

Silsesquioxane anions can be used to prepare functionalized silsesquioxanes. However, here too, the known processes are not economical. For example, ocktakis[trimethylsiloxy] octasilsesquioxane can be reacted in the presence of acid activated bleaching earth with 1,3-divinyl-1,1,3,3-tetramethyldisiloxane over long periods of time to prepare substituted silsesquioxanes bearing both trimethylsiloxy and vinyldimethylsiloxy groups. The product still bears non-functional trimethylsiloxy groups, even after 20 hours of reaction time, as indicated by Example 16 of U.S. Pat. No. 5,047,492. Other acidic catalysts such as acid (cationic) ion exchange resins have not been investigated, since octakis[trimethylsiloxy]octasilsesquioxane is known to suffer cleavage of the silsesquioxane cage, as disclosed by Hasegawaa et al., J. ORGANOMETALLIC CHEM., 441, p. 373 (1992), in which the above compound was exposed to Amberlyst® 15 cation exchange resin in heptane solution.

It would be desirable to provide a synthesis of polyhedral silsesquioxane anions, particularly the $Si_8O_{20}^{8-}$ anion, by methods which employ inexpensive starting materials and synthetic processes. It would be further desirable to provide processes for synthesizing functionalized derivatives of such compounds at reasonable cost.

SUMMARY OF THE INVENTION

It has now been surprisingly discovered that silica-rich byproducts from the combustion or pyrolysis of silica-containing natural organic products can serve as a low cost starting material for synthesis of polyhedral silsesquioxane anions. It has further been discovered that considerable reduction in reaction time and improved yield of functionalized polyhedral silsesquioxane derivatives can take place in water immiscible solvents. The products can, surprisingly, be converted to other functionalized derivatives via functional group exchange in the presence of ion exchange resins without suffering from destruction of the silsesquioxane cage.

DETAILED DESCRIPTION OF THE PREFERRED EMBODIMENT(S)

Suitable silica sources for use in the present invention include the pyrolysis or combustion residues from silica-containing organic substances such as crop residue, coal, coke, and the like. Most preferably, the source is rice hull ash or fly ash.

Rice hull ash is produced in large quantities by the combustion of rice hulls. As is well known, rice is an important staple crop in many parts of the world. Rice hulls are generally burned for their fuel value, and the ash remaining is land filled. Fly ash is generated by burning of coal and coal-derived products such as coke, and again is generally disposed of in land fills. Both these ashes are rich in silica, some of the silica in amorphous form, and some in crystalline form. Dissolution of silica into aqueous solution in the presence of bases such as quaternary ammonium compounds can be achieved at room temperature. The yield is maximized at higher than stoichiometric amounts of quaternary ammonium hydroxide, and reaction time decreases with increasing amounts of water, since the anion product is extensively hydrated. The reaction may be performed in mixtures of water and miscible alcohols such as methanol.

The foregoing method of preparing polyhedral silsesquioxane anions is not commercially viable, however, as the reaction occurs very slowly, even at high levels of quaternary ammonium compound and water. Moreover, product isolation is problematic, as the anions are quite soluble, particularly in water and water/methanol mixtures. Thus, considerable liquid must be removed by distillative techniques, spray drying, etc. Removal of large quantities of liquid is itself energy intensive. Rice hull ash has been converted by the above procedure to the octasilsesquioxane octaanion in nearly 90% yield based on soluble silica, which is generally about 50% by weight of total silica. This reaction, however, takes place over some 40-45 days, which is clearly not commercially viable. Prior syntheses using precipitated silica have taken place in aqueous methanol at room temperature or slightly above, most likely to avoid possible side reactions, including formation of sol-gels.

It has been surprisingly discovered that reaction time may be appreciably shortened to commercially viable reaction times by conducting the reaction under pressure at elevated temperatures, or by employing a solvent which has a higher boiling point at room temperature, or both. Since water is a necessary reactant, it is preferable that the reaction medium be able to dissolve some amount of water, preferably at least 4 mol water for each mol of soluble silica in the ash source. Thus, n-butanol has proven to be an acceptable solvent, in which the reaction can take place at ambient pressure at ca. 110° C. Under these conditions, the reaction can take place in as little as 8-12 hours. In general, high yields of 70-90% based on soluble silica, or higher, are obtained when the reaction temperature is maintained at greater than 60° C. It is only necessary that the solvent be able to dissolve all or part of the water which is required for the synthesis of the anions. Suitable alcohols include methanol, ethanol, n-propanol, i-propanol, n-butanol, 2-butanol, methoxyethanol, ethoxyethanol, methoxypropanol, and other alkoxyalcohols. The solvent must be capable of containing minimally 2 mol water per mol of soluble silica in the ash starting material, preferably 3 to 8 mol water on the same basis, and most preferably at least 4 mol water.

Use of the process described above leads to commercially viable reaction times, particularly in view of the low cost of the starting raw material. However, separation of the anion product may still be problematic, as the product is quite soluble in the reaction medium. Separation may be effected by removing solvent, cooling, and separating the precipitated product by customary methods such as centrifuging or filtration. The mother liquor still containing anion can then be recycled back to the reaction, all, or in part, to maximize the yield.

It has been unexpectedly discovered that proper selection of the quaternary ammonium compound can facilitate separation of the product. In this aspect of the invention, a quaternary ammonium compound other than tetramethylammonium hydroxide, and one which provides for only limited solubility of the anion product in the reaction mixture is selected. A suitable quaternary ammonium hydroxide compound can easily be selected by synthesizing the corresponding silsesquioxane anion in a laboratory scale or microscale batch and examining the solubility of the anion product. Preferably, the product will precipitate from the reaction mixture as it is formed, or upon cooling to a temperature in the range of 10° C. to 30° C. or higher. Tetramethylammonium hydroxide, for example, typically requires evaporation of considerable solvent as well as cooling to temperatures below 10° C. to precipitate product, both steps being energy intensive. The preferred quaternary ammonium compound is choline hydroxide, $[OH^-](CH_3)_3N^+CH_2CH_2OH$. Mixtures of a "precipitating" quaternary ammonium hydroxide and a quaternary ammonium hydroxide such as tetramethylammonium hydroxide may of course be used. When employed at higher temperatures in the range of 60° C. to 200° C., preferably 80° C. to 150° C., the increased solubility of all materials allows a more concentrated solution to be used, which facilitates precipitation of the product when employing a precipitating quaternary ammonium hydroxide. The particular ammonium hydroxide must be stable at the reaction temperature. Some quaternary ammonium compounds decompose at temperatures greater than 150° C., for example. In such cases, the reaction is conducted below the decomposition temperature.

The quaternary ammonium salt of the anion may be separated and optionally purified by conventional techniques. However, an advantage of the present invention is that the anion solution may often be used as such, particularly when in relatively concentrated form. A particular advantage of the choline hydroxide silsesquioxane salt product is that it contains fewer molecules of water of hydration (12) than the corresponding tetramethylammonium salt (24). Thus, use of quaternary ammonium hydroxides which produce anion salts with less than 24 mol of water of hydration is preferable.

The preparation of functionalized silsesquioxanes is a feature of one embodiment of the present invention. Functionalized silsesquioxanes are prepared by reaction of the anion with organochlorosilanes, preferably in at least stoichiometric ratio. This reaction may take place in aqueous solution, optionally with a cosolvent including but not limited to alcohols. The chlorosilane may be chosen among a wide variety of chlorosilanes, such as but not limited to, trimethylchlorosilane, vinyldimethylchlorosilane, dimethylchlorisilane, methylchlorosilane, cyclohexenyldimethylchlorosilane, allyldimethylchlorosilane, vinyldiphenylchlorosilane, vinylmethylphenylchlorosilane, methylphenylchlorosilane, glycidyldimethylchlorosilane, methacryloxydimethylchlorosilane, and other chlorosilanes. Of course, the corresponding bromosilanes can be used as well, although less available commercially. Dihalosilanes are also useful, but may result in linked functionalized silsesquioxanes, which may have advantages for certain applications.

Water is generally contained in the anion solution, either as part of the solvent mixture, or as water of hydration. Reaction of chlorosilanes with water leads to disiloxane byproducts. Since the boiling point of these disiloxanes is generally low, they can easily be removed by distillation. However, their formation removes valuable chlorosilane, thus requiring an amount of chlorosilane which is in stoichiometric excess based on the desired degree of reaction with the anion.

Several methods have been found which can be used to minimize the amount of chlorosilane-derived byproducts. In the first method, a solvent mixture which comprises a water-reactive "scavenger" is employed. The water scavenger may itself be the solvent, or may comprise a portion of the solvent. As water is released from the hydration cage, it reacts with the water scavenger, reducing the amount of water left to react with chlorosilane.

A second method of reducing byproduct disiloxane generation is to employ a non-aqueous solvent, and employ a silsesquioxane anion salt with less water of hydration, for example the choline hydroxide salt. These methods may, of course, be used in conjunction with each other.

Suitable water scavengers are, for example, acetals and hemiacetals which hydrolyze to form alcohols and ketones or aldehydes, preferably ketones. Such acetals and hemiacetals are well known, and include acetals prepared by reacting glycols such as ethylene glycol, propylene glycol, 2,3-dihydroxybutane, and like compounds with aldehydes or with ketones such as acetone, methylethylketone, cyclopentanone, and the like, and by the reaction of aldehydes or ketones with alcohols such as methanol, ethanol, n-propanol, i-propanol, n-butanol, and the like. A preferred water scavenger is 2,2-dimethoxypropane, which may also be used as a solvent. Even with such water scavengers, however, reaction with chlorosilane is often not stoichiometric.

A more effective method to achieve near stoichiometric reaction is to employ a heterogenous reaction mixture employing a poorly miscible or non-miscible solvent, i.e. a mixture of at least two solvents which form an at least two phase reaction medium. One solvent is a polar solvent such as water, alcohol, or mixtures thereof, or water and a water miscible organic solvent, and the second is a relatively non-polar organic solvent. Three or more solvents may be used if desired. The relatively non-polar chlorosilane is concentrated in the non-polar phase, while the unreacted anion and water are concentrated in the polar phase. As the anion reacts and becomes more soluble in the non-polar phase it accumulates in that phase. The non-polar phase can be separated, for example by decantation, and then solvent and unreacted chlorosilane removed by distillation. These latter can be recycled.

It has been found, however, that a single non-polar solvent medium can advantageously be employed. Such non-polar solvents include petroleum ether, light paraffinic solvents, hexane, heptane, toluene, etc. The water generated from the anion will phase separate. In some cases, gelation of the product may occur. In such cases, it is desirable to employ an organic carboxylic acid as a cosolvent/reactant, thus lowering the pH of the reaction medium and keeping it below a neutral pH where gelation of the products can occur. Suitable carboxylic acids include formic acid, acetic acid, trichloroacetic acid, and the like. It is noted that the acids employed react with base formed in or present in the reaction mixture, and do not serve any known catalytic role. Reaction of chlorosilanes themselves provide for formation some acid groups, but apparently not enough to control reaction pH. Aqueous acids are preferably not employed, as these have an adverse effect on the reaction. In lieu of the use of a non-polar solvent and organic acid, it is also possible to use only the organic acid, for example formic acid, as the reaction solvent. The product is generally insoluble, and precipitates from the reaction. When cosolvents are employed, the reaction product may remain in solution at the reaction temperature.

When fully functionalized silsesquioxanes are desired, the amount of chlorosilane on a mol to mol basis is generally at least n mols of chlorosilane, where n is the anionic charge of the silsesquioxane anion. Larger amounts may of course be used, particularly to speed up the reaction and ensure a more completely functionalized product. In general, from n to 8n mol of chlorosilane is used. Excess chlorosilane may be removed by distillation and reused or recycled. In the polyhedral silsesquioxanes of the invention, the approximate formula is $Si_nO_{sn-2}{}^{n-}$ where n is preferably from 6 to 12, more preferably 8. The formula is described as "approximate" since in addition to purely —O—$SiO_{3/2}$ siloxy groups, the "cage" may also contain or be bended to a minor quantity of $SiO_{212}$, $RSiO_{1/2}$, $RSiO_{3/2}$, $SiO_{4/2}$ units. In general, the polyhedral silsesquioxanes are those obtainable from natural ash sources, with or without addition of additional siloxy units during the preparation.

In a most preferred embodiment of the invention, an essentially monophasic mixture of substantially non-polar solvent such as hexane is used in conjunction with an organic acid such as formic acid. The preferred ratio of organic acid to anion is 4:1 to 1:4, more preferably 3:1 to 1:1, and most preferably about 2:1. If too low an amount is employed, gels insoluble in the non-polar solvent may be formed. The amount required is preferably at least equal to the amount whereby no gel or minimal gel content is produced, preferably a larger amount.

In a further embodiment of the present invention, an elegant synthesis of functionalized silsesquioxanes is accomplished by first forming a desired and preferably relatively stable first functionalized silsesquioxane, and exchanging functional groups to produce a second functionalized silsesquioxane in the presence of a synthetic acid ion exchange catalyst. Amberlyst® 15 cation exchange resin catalyst is preferred. The second functional groups are provided by a di- or polysiloxane, preferably a disiloxane. Examples of the latter include tetramethyldisiloxanes bearing vinyl groups, Si-bonded hydrogen, epoxy groups such as glycidyl groups, allyl groups, ω-hexenyl groups, and the like.

In this embodiment of the invention, the first functionalized silsesquioxane is preferably one prepared from the corresponding anion as previously described, but may also be prepared by other techniques such as those based on hydrolysis of tetraethylsilicate. The first functionalized silsesquioxane is preferably one which is chemically stable and preferably easily purified and characterized. Octakis[trimethylsiloxy]octasilsesquioxane is a preferred first functionalized silsesquioxane.

The first functionalized silsesquioxane may be dissolved in non-polar solvent or preferably, in the disiloxane to be employed. Thus, for example, octakis [trimethylsiloxy]octasilsesquioxane may be dissolved in 1,1,3,3-tetramethyldisiloxane or 1,3-divinyl-1,1,3,3-tetramethyldisiloxane, and the solution passed through a column containing ion exchange resin. Conventional batch processes such as a stirred reaction vessel may also be used. The reaction generally produces an equilibrium mixture of substituted silsesquioxanes bearing both first and second functional groups. If complete substitution is required, either a large excess of disiloxane must be employed, or an iterative process may be employed where a partially second-functionalized product is reacted with additional disiloxane. For complete reaction with a single stage reaction, for example, a ratio of second functional group to first functional group of greater than 400, preferably greater than 800 may be employed. Mixtures of different disiloxanes may be used to produce polyhedral silsesquioxanes with mixed functionality.

Reaction by products are mixed siloxanes containing both functional groups, such as pentamethyldisiloxane, and disiloxanes containing two first functional groups, such as hexamethyldisiloxane. These may be separated from the solvent disiloxane by distillation and the latter recycled. Since the boiling points of the disiloxanes are relatively low, the process is not overly energy intensive. However, the benefit of the process is the preparation of functionalized silsesquioxanes which are difficult or impossible to prepare directly from the anion, for example because of reactivity of the functional groups under the reaction conditions.

During the synthesis of the quaternary ammonium salts of the polyhedral silsesquioxane anions, T-unit precursors such as trichlorosilanes and trialkoxysilanes may be added. The addition of these T-unit precursors may alter the structure of the anions by incorporating $RSiO_{3/2}$ units which can be incorporated within the silsesquioxane cages per se, or may link silsesquioxane cages together. The net result is predominantly an alteration of the physiochemical properties of the product. For example, long chain hydrocarbon groups may be implemented by adding chlorosilanes such as n-octyltrichlorosilane. By the same token, minor amounts of D units may be incorporated, for example by including compounds such as bis(n-octyl)dichlorosilane in the synthesis.

The anion solutions also have utility in treating wood. Wood can be impregnated by spraying, immersion, or by immersion under pressure. The anions may be applied in alcohol solvent or other solvents in which they are soluble. Immersion in boiling solution of anion in alcohol or other solvent is suitable, for example. The resulting silicified product is harder, more dense, and also fire resistant. It should be noted that solutions of the corresponding alkali metal salts do not generally provide acceptable results.

Having generally described this invention, a further understanding can be obtained by reference to certain specific

Example 1

Synthesis of $Si_8O_{20}^{8-}$ from Rice Hull Ash

A 45% methanolic choline hydroxide solution 9218 mL, 1.70 mol) is poured into a 1000 mL round-bottom flask containing milled rice hull ash (60.491 g, 0.998 mol), n-butanol (300 mL, 3.28 mol) and water (72.0 mL, 4.00 mol) equipped with a magnetic stirrer. The reaction vessel is also equipped with a condenser and flushed with nitrogen. The reaction mixture is heated to 100° C. for 8-12 h. The dark brown octaanion solution is filtered from the thick slurry of residual rice hull ash with celite. The residual rice hull ash is then washed several times with methanol (approximately 30 mL). Upon cooling, white crystals of the choline salt of the octaanion form. The solid crystals are filtered from solution, dried in air and can be recrystallized from hot water. Yield is determined by conversion to $Si_8O_{20}[Si(CH_3)_3]_8$ as indicated below. The synthesis is not optimized.

Trimethylchlorosilane (21.8 mL, 0.1999 mol) and hexane (125.0 mL) are poured into a 500 mL Schlenk flask equipped with an addition funnel, reflux condenser and magnetic stirrer. The reaction flask is carefully flushed with $N_2$ and cooled in an ice bath to 0° C. The rice hull octaanion solution (50.0 mL) from choline hydroxide in butanol is added dropwise through the addition funnel over 30 minutes. The reaction is allowed to stir for an additional 30 minutes. To isolate the $Si_8O_{20}[Si(CH_3)_3]_8$ product, the reaction mixture is transferred to a separatory funnel and the organic layer recovered. The aqueous layer is extracted twice with 75 mL of hexane. The combined hexane layers are then dried over $Na_2SO_4$. The hexane solvent is removed by rotary evaporation to give a white, powdery solid (3.08 g, 41.0% based on the 50 mL from the original reaction solution). The total yield per the entire reaction solution would be 24.7 g.

Example 2

Synthesis of $Si_8O_{20}[Si(CH_3)_2H]_8$ by the Stoichiometric Reaction of $Si_8O_{20}^{8-}$ with Dimethylchlorosilane A typical reaction is carried out as follows. Solid (2-hydroxyethyl) trimethylammonium silicate is prepared as above, and then dissolved in 1 mL of methanol. $Si_8O_{20}^{8-}$ is the only silicate anion found in the methanol solution ($SiO_2$ concentration 1.38 mol/L) and is stable in solution even 7 days after the preparation. Thus, the stoichiometric amount of dimethylchlorosilane required for producing $Si_8O_{20}[Si(CH_3)_2H]_8$ from $Si_8O_{20}^{8-}$ in the solution is calculated to 0.49 mL.

The methanol solution was added dropwise to a mixture of 3 mL of formic acid, 0.25 mL of hexane, and 0.49 mL of dimethylchlorosilane, which is stirred for 5 min for intimate mixing prior to the addition. The mixture is stirred for 1 h at 20° C. at ambient pressure. A portion of the product precipitates from the solution during the reaction. Hexane is added to the mixture after the reaction. The precipitates dissolve and the mixture is separated into two phases, a hexane phase and an aqueous phase, by the addition of hexane.

Low boiling components of the hexane phase (mainly hexane) are removed by a rotary vacuum evaporator to obtain solids which are then washed with acetonitrile. Most of the solids are insoluble in acetonitrile, but are soluble in tetrahydrofuran, acetone, and hexane.

A tetrahydrofuran solution of the product which remain as solids after washing with acetonitrile gives rise to one peak at 12.5 min in the gas chromatogram. Analytical conditions for gas chromatography (GC) are described in Y. D. Blum et al., "Process for Making Ceramic Materials," U.S. Pat. No. 5,017,529, May 21, 1991. The $^{29}Si$ NMR spectrum of a tetrahydrofuran-$d_8$ solution of the product gives two signals at −3.00 and −110.34 ppm, ascribable to the (SiO)$_3$ SiOSi (CH$_3$)$_2$H and SiOSi(CH$_3$)$_2$H units, respectively. (Chemical shifts for $^1H$, $^{13}C$, and $^{29}Si$ NMR spectroscopy are given with reference to tetramethylsilane external standard.) These values are in accordance with those reported by Hoebbel et al.

Two signals are observed at 4.73 and 0.25 ppm in the $^1H$ NMR spectrum, which can be assigned to Si(CH$_3$)H (1H) and Si(CH$_3$)$_2$H (5.8H), respectively, indicating that the compound possesses an Si—H bond and that the ratio of H atoms in the Si—CH$_3$ group to those in the Si—H group is ca. 6. The $^{13}C$ NMR spectrum gives rise to one signal at 0.00 ppm which is attributable to Si(CH$_3$)$_2$H. In addition, the [M−1 (H)]$^+$ peak appears at m/z=1015 in the mass spectrum of the compound by EI. These suggest that the product is $Si_8O_{20}[Si(CH_3)_2H]_8$, indicating that the reaction of $Si_8O_{20}^{8-}$ with dimethylchlorosilane in the mixture of formic acid and hexane affords $Si_8O_{20}[Si(CH_3)_2H]_8$. The isolation yield of $Si_8O_{20}[Si(CH_3)_2H]_8$ is 74%.

A small amount of solids are obtained from the acetonitrile washings as well. The solids are found to be a mixture of three compounds by GC. In the $^{29}Si$ NMR spectrum of a THF-$d_8$ solution of the products, signals appear in three regions centered around −4, −104, and −113 ppm, which can be assigned to the SiOSi(CH$_3$)$_2$H, (SiO)$_3$Si(O—), and Si(OSi)$_4$ units, respectively. The [M−1]$^+$ peak of the compounds is observed at m/z=841, 899, and 957 in the mass spectrum. In addition, when a mixture prepared by dissolving the solids in dimethylchlorosilane is stirred for 1 D at room temperature, the gas chromatogram of the mixture after the reaction gives rise to only one peak due to $Si_8O_{20}[Si(CH_3)_2H]_8$, indicating that $Si_8O_{20}[Si(CH_3)_2H]_8$ forms from the three compounds, in other words, the compounds consist of the $Si_8O_{20}^8$ silicate core. These suggest that the compounds would be $Si_8O_{20}[Si(CH_3)_2H]_{8-n}(H)_n$ (n=1-3), the incompletely dimethylsilylated derivatives of $Si_8O_{20}^{8-}$ possessing both the dimethylsily and silanol groups. Although the reaction gives a small amount of the incompletely dimethylsilylated derivatives as by-products, these can be removed by washing with acetonitrile.

The reaction of $Si_8O_{20}^{8-}$ with dimethylchlorosilane was investigated as a function of the amount of formic acid. When the amount of formic acid is smaller than 3 mL, gels form which are insoluble in hexane. Their amount increases with decreasing amount of formic acid. This indicates that the reaction system is not acidic enough when the amount of formic acid is smaller than 3 mL, which causes the $Si_8O_{20}^{8-}$ silicate anion to polymerize to form gels. Because of gel formation, products soluble in hexane, $Si_8O_{20}[Si(CH_3)_2H]_{8-n}(H)_n$ (n=0-3), decreases with decreases in formic acid used. When the amount is greater than 3 mL, gels do not form and the product yield is constant.

It is particularly difficult to carry out reactions using formic acid only, as reproducibility is poor; since $Si_8O_{20}[Si(CH_3)_2H]_{8-n}(H)_n$ (n=0-3) species are not soluble in formic acid. Thus, hexane is preferably added to dissolve $Si_8O_{20}[Si(CH_3)_2H]_{8-n}(H)_n$ (n=0-3).

The yield of $Si_8O_{20}[Si(CH_3)_2H]_8$ does not vary when the amount of hexane is increased up to 0.5 ml, with the amount of formic acid fixed at 3 mL. When the reaction is carried out using more than 1 ml of hexane, however, its yield decreases and instead the amounts of $Si_8O_{20}[Si(CH_3)_2H]_{8-n}(H)_n$ (n=1-3) increase. This likely is due to decreased concentration of dimethylchlorosilane in the reaction mixture with an increase in the amount of hexane.

The effect of the reaction temperature affects the yield of $Si_8O_{20}[Si(CH_3)_2H]_8$. The yield is highest when the temperature is set at 20° C. The amounts of $Si_8O_{20}[Si(CH_3)_2H]_{8-n}(H)_n$ (n=1-3) increases and that of $Si_8O_{20}[Si(CH_3)_2H]_8$ decreases when the reaction is carried out at 10° C. or 30° C.

The above-mentioned reaction conditions, that is, the amounts of formic acid and hexane and the reaction temperature, are applicable for the stoichiometric reaction of the $Si_8O_{20}^{8-}$ silicate anion with other monochlorosilanes such as trimethylchlorosilane. The isolation yield of $Si_8O_{20}[Si(CH_3)_3]_8$ thus synthesized is 81%. In addition, trichloroacetic acid may be used instead of formic acid. In this case, is preferable to use no less than 0.35 g of trichloroacetic acid to prevent the gelation of the reaction mixture and produce $Si_8O_{20}[Si(CH_3)_2H]_8$.

Although the amount of the by-products $\{Si_8O_{20}[Si(CH_3)_2H]_{8-n}(H)_n$ (n=1-3)$\}$, recovered as soluble products in acetonitrile, is small, if necessary, the by-product can be converted into $Si_8O_{20}[Si(CH_3)_2H]_8$ by the following two methods: (1) dissolve in an excess amount of dimethylchlorosilane and stir for 1-2 d (depending on the amount of the by-products) and (2) dissolve in 1,1,3,3-tetramethyldisiloxane, and Amberlyst 15 cation-exchange resin in the solution, and allow the solution to stand at room temperature for at least 1 d. The time is not critical, and can be altered by changing the temperature or the amount of ion exchange resin, for example.

Example 3

Synthesis of $Si_8O_{20}[Si(CH_3)_2H]_8$ by Substitution of the Trimethylsilyl Group in $Si_8O_{20}[Si(CH_3)_3]_8$ for the Dimethylsilyl Group A typical reaction is carried out as follows. $Si_8O_{20}[Si(CH_3)_3]_8$ (9.45 mg) is dissolved in 1,1,3,3-tetramethyldisiloxane (6.5 mL), followed by the addition of Amberlyst 15 cation-exchange resin (0.15 g). The 1,1,3,3-tetramethyldisiloxane solution of $Si_8O_{20}[Si(CH_3)_3]_8$ is stirred vigorously for 26 h at room temperature under ambient pressure.

GC of the solution after 26 h gives one peak with a retention time of 12.5 min, while $Si_8O_{20}[Si(CH_3)_3]_8$ (the starting material) gives a peak at 13.7 min. Amberlyst 15 cation-exchange resin is filtered off, and the filtrate is removed by rotary evaporation to obtain a transparent solid, soluble in usual organic solvents including tetrahydrofuran, acetone, and hexane. Two sharp signals appear at −3.00 and −110.34 ppm in the $^{29}Si$ NMR spectrum of a tetrahydrofuran-$d_8$ solution of the product, ascribable to the $(SiO)_3SiOSi(CH_3)_2H$ and $SiOSi(CH_3)_2H$ units, respectively, and the $[M-1]^+$ peak appears at m/z=1015 in the mass spectrum, indicating that the product is $Si_8O_{20}[Si(CH_3)_2H]_8$.

Even if the reaction is conducted for 100 h under the same conditions, $Si_8O_{20}[Si(CH_3)_2H]_8$ is essentially the only product and no other compounds are detected by GC. This suggests that no breakdown of the silicate core of $Si_8O_{20}[Si(CH_3)_3]_8$ takes place during the reaction. The yield of $Si_8O_{20}[Si(CH_3)_2H]_8$ is 98% (based on the amount of $Si_8O_{20}[Si(CH_3)_3]_8$ employed), as determined with GC using tetradecane as an internal standard.

To investigate the reaction process, the reaction is evaluated by GC. The gas chromatogram of the solution after 12 h of reaction gives 7 additional peaks at constant intervals of retention time between the peaks due to $Si_8O_{20}[Si(CH_3)_2H]_8$ and $Si_8O_{20}[Si(CH_3)_3]_8$.

In the $^{29}Si$ NMR spectrum of a THF-$d_8$ solution of a mixture of the nine compounds gives rise to signals in three narrow regions (<ca. 1 ppm) around 11, −3, and −110 ppm, attributable to the $SiOSi(CH_3)_3$, $SiOSi(CH_3)_2H$, and $(SiO)_3SiOSi(CH_3)_2Y$ (Y==$CH_3$ or H) units, respectively. In the mass spectra of compounds corresponding to the additional 7 peaks, the $[M-1]^+$ ion is observed at m/z=1029, 1043, 1057, 1071, 1085, 1099, and 1113. These facts indicate that the 7 additional peaks are due to $Si_8O_{20}^{8-}$ structure-based compounds possessing both the dimethylsilyl and trimethylsilyl group, $Si_8O_{20}[Si(CH_3)_2H]_{8-n}[Si(CH_3)_3]_n$ (n=1-7).

Intensities of the peaks in the gas chromatogram vary with the reaction time, and the peak due to $Si_8O_{20}[Si(CH_3)_2H]_8$ becomes dominant after 26 h. This indicates that $Si_8O_{20}[Si(CH_3)_2H]_{8-n}[Si(CH_3)_3]_n$ (n=1-7) are intermediates in the formation of $Si_8O_{20}[Si(CH_3)_2H]_8$ from $Si_8O_{20}[Si(CH_3)_3]_8$ and that the substitution reaction completes at 26 h under these conditions.

When the reaction is carried out using various amounts of $Si_8O_{20}[Si(CH_3)_3]_8$ by keeping the amounts of 1,1,3,3-tetramethyldisiloxane and Amberlyst 15 cation-exchange resin constant at 6.5 cm³ and 0.15 g, respectively, compounds possessing both the dimethylsilyl and trimethylsilyl group are present together with $Si_8O_{20}[Si(CH_3)_2H]_8$ in the solutions prepared with more than 9.45 mg of $Si_8O_{20}[Si(CH_3)_3]_8$ even if the reaction time is prolonged to 100 h. $Si_8O_{20}[Si(CH_3)_2H]_8$ forms exclusively in solutions prepared with not more than 9.45 mg of $Si_8O_{20}[Si(CH_3)_3]_8$. The distribution of $Si_8O_{20}[Si(CH_3)_2H]_{8-n}[Si(CH_3)_3]_n$ (n=0-8) in solutions after 100 h of stirring depends on the ratio of $Si_8O_{20}[Si(CH_3)_3]_8$ to 1,1,3,3-tetramethyldisiloxane employed for the reaction.

To express the ratio of amounts of $Si_8O_{20}[Si(CH_3)_3]_8$ and 1,1,3,3-tetramethyldisiloxane, a DMS/TMS ratio can be used, which indicates the ratio of number of dimethylsilyl groups in 1,1,3,3-tetramethyldisiloxane to that of trimethylsilyl groups in $Si_8O_{20}[Si(CH_3)_3]_8$ which are used to prepare the starting solution. The DMS/TMS ratio of the solution prepared with 9.45 mg of $Si_8O_{20}[Si(CH_3)_3]_8$ and 6.5 cm³ of 1,1,3,3-tetramethyldisiloxane is 1100. Thus, it can $Si_8O_{20}[Si(CH_3)_2H]_8$ forms exclusively from solutions with DMS/TMS ratios over 1100.

This reaction can be scaled up easily to produce larger amounts of $Si_8O_{20}[Si(CH_3)_2H]_8$ by adjusting the DMS/TMS ratio of the starting solutions over 1100. For example, a solution prepared by dissolving 0.0836 mmol of $Si_8O_{20}[Si(CH_3)_3]_8$ in 65 cm³ of 1,1,3,3-tetramethyldisiloxane (the amount of Amberlyst 15 cation resin employed: 1.5 g) gave 0.0752 mmol $Si_8O_{20}[Si(CH_3)_2H]_8$ which means that the isolation yield of $Si_8O_{20}[Si(CH_3)_2H]_8$ is 89.9%.

The amount of Amberlyst 15 cation-exchange resin did not affect the extent of reaction but it does effect the completion time. Greater amounts of resin provide faster reaction rates and therefore shorter reaction times, as expected of a catalyst. Continuous reactions in packed tubular reactors or series-connected CTSRs are thus possible.

The filtrate is found to consist of 1,1,3,3-tetramethyldisiloxane $\{[M-1]^+$, m/z=133$\}$, pentamethyldisiloxane $[H(CH_3)_2Si\text{---}O\text{---}Si(CH_3)_3]\{[M-1]^+$, m/z=147$\}$, and hexamethyldisiloxane $\{[M-15(CH_3)]+$, m/z=147$\}$ by means of mass spectrometry. These compounds are easily separated by distillation. The recovered 1,1,3,3-tetramethyldisiloxane can be recycled and used to synthesize $Si_8O_{20}[Si(CH_3)_2H]_8$ by the above mentioned reaction. Amberlyst 15 cation-exchange resin can be used repeatedly by heating at 100° C. for over 4 h prior to use, as described above. In addition, hexamethyldisiloxane recovered from the solvent can be used to prepare Si₈O₂₀[Si(CH₃)₃]₈ (the starting material) from the Si₈O₂₀⁸⁻ silicate anion by the trimethylsilylation technique developed by Lentz, C. W. Lentz, INORG. CHEM., 3, 574 (1964). Pentamethyldisiloxane can be recycled by disproportionation over the Dowex® catalyst.

In addition, it is possible to produce Si₈O₂₀[Si(CH₃)₂(CH=CH₂)]₈ from Si₈O₂₀[Si(CH₃)₃]₈ on the basis of this reaction, although it was described that the reaction of Si₈O₂₀[Si(CH₃)₃]₈ with 1,3-divinyl-1,1,3,3-tetramethyldisiloxane under the presence of acid-activated bleaching earth gave a mixture of Si₈O₂₀[Si(CH₃)₂(CH=CH₂)]ₓ[Si(CH₃)₃]₈₋ₓ in U.S. Pat. No. 5,047,492.

Example 4

Synthesis of Si₈O₂₀[Si(CH₃)₂(CH=CH₂)]₇[Si(CH₃)₃] from Si₈O₂₀[Si(CH₃)₃]₈

Si₈O₂₀[Si(CH₃)₃]₈ can be reacted with 1,3-divinyl-1,1,3,3-tetramethyldisiloxane at a VDMS/TMS ratio (the ratio of number of vinyldimethylsilyl groups in 1,3-divinyl-1,1,3,3-tetramethyldisiloxane to that of trimethylsilyl groups in Si₈O₂₀[Si(CH₃)₃]₈) of 1100 under the presence of Amberlyst 15 cation-exchange resin at room temperature, Si₈O₂₀[Si(CH₃)₂(CH=CH₂)]₇[Si(CH₃)₃] is present together with Si₈O₂₀[Si(CH₃)₂(CH=CH₂)]₈ even if the reaction time is prolonged to 100 h. By pursuing the reaction with gas chromatography, it is found that the reaction rate for the formation of Si₈O₂₀[Si(CH₃)₂(CH=CH₂)]₈ appears to slow down after around 50 h. In addition, hexamethyldisiloxane and vinylpentamethyldisiloxane are found to form as by-products during the reaction.

The lowering of the reaction rate may result from a reverse reaction, that is, substitution of the vinyldimethylsilyl group formed on the Si₈O₂₀⁸⁻ silicate core for the trimethylsilyl group because of the presence of the by-products in reaction mixture. Since the b.p. of hexamethyldisiloxane and vinylpentamethyldisiloxane is 101 and 120° C., respectively, which is lower that that of 1,3-divinyl-1,1,3,3-tetramethyldisiloxane (139° C.), they can easily be removed from the reaction mixture by heating. With this treatment, that is, removal of the by-products by heating during the reaction, Si₈O₂₀[Si(CH₃)₃]₈ can be converted into Si₈O₂₀[Si(CH₃)₂(CH=CH₂)]₈ solely. The isolation yield of Si₈O₂₀[Si(CH₃)₂(CH=CH₂)]₈ is 94.0%.

Example 5a

Synthesis of Tetrakis(dimethylsiloxy)tetrakis(dimethylethylpehnylsiloxy)octasilsesquioxane; TPTHOS from Si₈O₂₀[Si(CH₃)₂H]₈

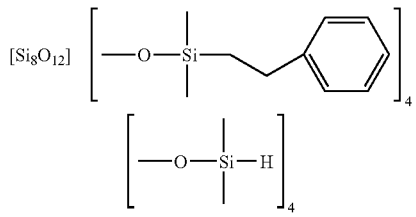

To 100 ml schlenk flask with reflux condenser is added octakis[dimethylsiloxy]octasilsesquioxane as prepared previously (10.18 g, 0.01 mol). The flask is subjected to vacuumed to evacuate oxygen and water from the system. THF 25 ml, Styrene (4.21 g, 0.04 mol) and 2 mM Pt(dvs) toluene solution (0.1 ml) as a hydrosilylation catalyst are added and heated at 80° C. for 3 h in N₂ atmosphere. After cooling to room temperature, the solution is concentrated and dried under reduced pressure (1 mm Hg/40° C.) to provide a pale yellow transparent viscous liquid. Yield: 98.4% of theoretical. Analytical characterization is as follows. ¹H NMR:

| | | |
|---|---|---|
| a: 0.10 ppm, 2.3H | b: 0.19 ppm, 5.4H | c: 0.27 ppm, 6.7H |
| d: 1.04 ppm, 1.7H | e: 1.44 ppm, 1.1H | f: 2.33 ppm, 0.4H |
| g: 2.74 ppm, 1.7H | h: 4.79 ppm, 1.0H | i: 7.16 ppm, 5.7 H |

α-substitution/β-substitution=2.3, Si—C/Si—H=4.2/3.8

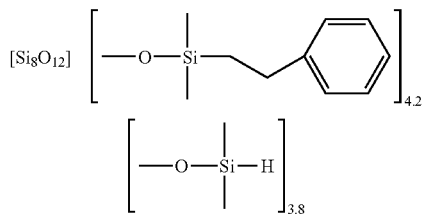

DTA-TGA in air: Ceramic Yield: 65.0% Theoretical yield: 66.7%

Example 5b

Tetrakis[dimethylpropylaminosiloxy]tetrakis[dimethylethylphenylosiloxy]octasilses Quioxane; TATPOS from TPTHOS

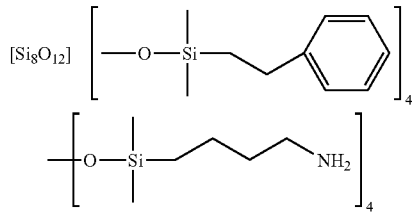

To 100 ml schlenk flask with reflux condenser is added Tetrakis(dimethylsiloxy)tetrakis(dimethylethylphenylsiloxy)octasilisesquioxane (TPTHOS, 5.21 g, 0.0036 mol) and PtO₂ (0.1 g, 1×10⁻⁵ mol) as a catalyst. The system is degassed under vacuum. To the system are added 5 ml toluene 5 ml and allylamine (1.62 ml, 0.022 mol) and heated 100° C. for 5 h in N₂ atmosphere. After cooling to room temperature, the reactant is filtered through activated carbon/celite to remove the catalyst. The filtrate is concentrated and dried under pressure (1 mmHg/room temperature) to provide a viscous yellow transparent liquid. Yield: 86% of theoretical. Characterization by ¹H NMR:

Si—CH₃: 0.12-0.22 ppm, 12H

| | | |
|---|---|---|
| a: 0.65 ppm, 0.8H | b: 1.04 ppm, 1.9H | c: 1.47 ppm, 1.2H |
| d: 1.70 ppm, 1.0H | e: 2.32 ppm, 1.0H | f: 2.74 ppm, 1.6H |
| g: 3.20 ppm, 1.0H | h: 7.15-7.24 ppm, 5.9 H | |

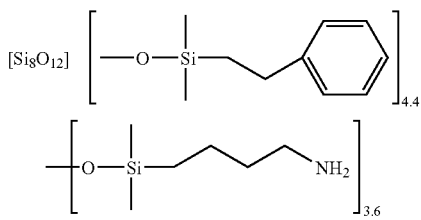

DTA-TGA in air. Ceramic Yield: 59.1% Theoretical yield: 57.6%

Example 6

Tetrakis[trifluorhexyl]tetrakis[dimethylethylphenylosiloxy]octasilsesquioxane

To a 100 ml Schlenk flask with reflux condenser is added octadimethylsiloxyoctasilsesquioxane. The system is degassed under vacuum. To the system are added 5 ml toluene, 5 ml trifluorohexene, and AIBN. The reaction is heated at 100° C. for 5 h in $N_2$ atmosphere. After cooling to room temperature, the reactant is filtered through activated carbon/celite to remove catalyst. The filtrate is concentrated and dried under pressure (1 mm/room temperature) to provide a viscous yellow transparent liquid that consisted of a mixture of fluorohexyl substituted species with the tetrakis material being the major component.

Example 7

To a 500 mL flask was added 250 mL of octaanion-tetramethylammoniumhydroxide-methanol solution and 3 pine wood samples, each 7.5 cm long by 1 cm dia. The solution plus samples was refluxed for 18 h. The wood samples were removed from the solution and dried at 100° C. for 24 h to remove absorbed methanol. The weight increase is 10% (0.3 g average) per wood sample. Samples thus treated when subjected to a propane gas torch will combust, however, combustion ceases after the torch is removed whereas an untreated piece of wood continues to burn.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. A process for preparing a functionalized silsesquioxane, comprising:
    a) preparing a quaternary ammonium salt of a polyhedral silsesquioxane anion of the formula $Si_nO_{5n/2}{}^{n-}$ comprising:
        i) providing a silica source derived from the combustion of naturally occurring organic substances;
        ii) reacting said silica source with water and quaternary ammonium hydroxide in an alcohol solvent at a temperature in excess of 60° C.; and
    b) reacting said quaternary ammonium salt with one or more organochlorosilanes in a liquid to form an organosiloxy-functionalized silsesquioxane, wherein said liquid comprises a water scavenger.

2. The process of claim 1, wherein said water scavenger comprises an acetal or hemiacetal.

3. A process for preparing a functionalized silsesquioxane, comprising:
    a) preparing a quaternary ammonium salt of a polyhedral silsesquioxane anion of the formula $Si_nO_{5n/2}{}^{n-}$, including:
        i) providing a silica source derived from the combustion of naturally occurring organic substances;
        ii) reacting said silica source with water and quaternary ammonium hydroxide in an alcohol solvent at a temperature in excess of 60° C.; and
    b) reacting said quaternary ammonium salt with one or more organochlorosilanes in a liquid to form an organosiloxy-functionalized silsesquioxane, wherein said liquid comprises a liquid organic acid.

4. A process for preparing a functionalized silsesquioxane, comprising:
    a) preparing a quaternary ammonium salt of a polyhedral silsesquioxane anion of the formula $Si_nO_{5n/2}{}^{n-}$, including:
        i) providing a silica source derived from the combustion of naturally occurring organic substances;
        ii) reacting said silica source with water and quaternary ammonium hydroxide in an alcohol solvent at a temperature in excess of 60° C.; and
    b) reacting said quaternary ammonium salt with one or more organochlorosilanes in a liquid to form an organosiloxy-functionalized silsesquioxane, wherein said liquid comprises a non-polar organic solvent and an organic acid.

5. The process of claim 4, further comprising removing an organic phase and separating non-polar organic solvent by means of distillation.

6. A process for the preparation of a functionalized silsesquioxane, comprising:
    a) preparing a polyhedral silsesquioxane with a first siloxy functionality, including:
        aa) preparing a quaternary ammonium salt of a polyhedral silsesquioxane anion of the formula $Si_nO_{5n/2}{}^{n-}$ including:
            i) providing a silica source derived from the combustion of naturally occurring organic substances:
            ii) reacting said silica source with water and quaternary ammonium hydroxide in an alcohol solvent at a temperature in excess of 60° C.; and
        bb) reacting said quaternary ammonium salt with one or more organochlorosilanes in a liquid to form an organosiloxy-functionalized silsesquioxane;
    b) contacting said polyhedral silsesquioxane with said first siloxy functionality in a solvent with a disiloxane containing siloxy groups of a second functionality in the presence of a synthetic cation exchange resin; and
    c) isolating a silsesquioxane containing second siloxy functional groups.

7. The process of claim 6, wherein said solvent comprises said disiloxane containing siloxy groups of a second functionality.

8. The process of claim 6, wherein said disiloxane containing said siloxy groups of a second functionality comprises a disiloxane containing Si-vinyl groups, Si-allyl groups, Si—H groups, or Si-epoxy groups.

9. A process for the preparation of a functionalized silsesquioxane, comprising:
    a) preparing a polyhedral silsesquioxane with a first siloxy functionality, including:

aa) preparing a quaternary ammonium salt of a polyhedral silsesquioxane anion of the formula $Si_nO_{5n/2}{}^{n-}$, including:
  i) providing a silica source derived from the combustion of naturally occurring organic substances;
  ii) reacting said silica source with water and quaternary ammonium hydroxide in an alcohol solvent at a temperature in excess of 60° C.; and
bb) reacting said quaternary ammonium salt with one or more organochlorosilanes in a liquid to form an organosiloxy-functionalized silsesquioxane;

b) contacting said polyhedral silsesquioxane with said first siloxy functionality in a solvent with a disiloxane containing siloxy groups of a second functionality in the presence of a synthetic cation exchange resin; and c) isolating a silsesquioxane containing second siloxy functional groups, wherein said silsesquioxane with a first siloxy functionality comprises octakis octasilsesquioxane.

* * * * *

UNITED STATES PATENT AND TRADEMARK OFFICE
CERTIFICATE OF CORRECTION

PATENT NO. : 7,576,169 B2  Page 1 of 1
APPLICATION NO. : 10/971809
DATED : August 18, 2009
INVENTOR(S) : Hasegawa et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1253 days.

Signed and Sealed this

Seventh Day of September, 2010

David J. Kappos
*Director of the United States Patent and Trademark Office*